(12) United States Patent
Dierker et al.

(10) Patent No.: US 8,821,844 B2
(45) Date of Patent: Sep. 2, 2014

(54) POLY-α-OLEFIN-CONTAINING COSMETIC COMPOSITION

(71) Applicant: Cognis IP Management GmbH, Düsseldorf (DE)

(72) Inventors: Markus Dierker, Düsseldorf (DE); Daniela Prinz, Dormagen (DE); Alfred Westfechtel, Hilden (DE); Lars Zander, Rommerskirchen (DE); Achim Ansmann, Erkrath (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 13/953,959

(22) Filed: Jul. 30, 2013

(65) Prior Publication Data

US 2013/0317119 A1 Nov. 28, 2013

Related U.S. Application Data

(63) Continuation of application No. 10/553,182, filed as application No. PCT/EP2004/003699 on Apr. 7, 2004, now Pat. No. 8,518,386.

(30) Foreign Application Priority Data

Apr. 16, 2003 (DE) .................... 103 17 781

(51) Int. Cl.
   *A61K 8/72* (2006.01)
   *A61K 8/02* (2006.01)
   *A61K 8/81* (2006.01)

(52) U.S. Cl.
   CPC ....................................... *A61K 8/81* (2013.01)
   USPC ...................................... 424/70.11; 424/401

(58) Field of Classification Search
   None
   See application file for complete search history.

(56) References Cited

U.S. PATENT DOCUMENTS

| | | | |
|---|---|---|---|
| 4,060,569 A | 11/1977 | Woods et al. | |
| 5,747,009 A * | 5/1998 | Hansenne | ........................ 424/59 |
| 6,464,967 B1 | 10/2002 | Collin | |
| 6,641,821 B1 | 11/2003 | Collin et al. | |
| 2004/0267073 A1* | 12/2004 | Zander et al. | .................. 585/533 |

FOREIGN PATENT DOCUMENTS

| | | | |
|---|---|---|---|
| DE | 10152267 | 4/2003 | |
| EP | 0533393 | 3/1993 | |
| EP | 0547897 | 6/1993 | |
| EP | 0804921 | 11/1997 | |
| JP | 2005194184 | 8/1993 | |
| JP | 2005-255039 | 10/1993 | |
| JP | 2000515562 | 11/2000 | |
| JP | 2000-95644 | 4/2004 | |
| JP | 2008508282 | 3/2008 | |
| WO | WO-99/62468 | 12/1999 | |
| WO | WO-03/035707 | 5/2003 | |
| WO | WO 03/035707 | * 5/2003 | .............. C08F 10/00 |
| WO | WO-2004/078336 | 9/2004 | |

OTHER PUBLICATIONS

Kosmetikverordnung, Appendix 6, Parts A and B, *Deutsches Institut fur Korperpflege und Hygiene e.V.*, 2013.
Cognis Deutschland GmbH & Co. KG, PCT/EP02/11392, May 1, 2003.
Zeidler, U., "Uber das Spreiten von Lipiden auf der Haut", *Fette, Seifen, Anstrichmittel*, vol. 87 1985, 403-408.

* cited by examiner

*Primary Examiner* — Brian Gulledge
(74) *Attorney, Agent, or Firm* — Servilla Whitney LLC

(57) ABSTRACT

The invention is directed to a cosmetic composition which contains at least one poly-α-olefin produced by subjecting at least one primary alcohol to dehydrating polymerization at a temperature of 60° C. to 340° C. in the presence of acidic alumino layer silicates. The primary alcohol is an alcohol from the group of unsaturated monofunctional alcohols, branched monofunctional alcohols and difunctional alcohols. The poly-α-olefin is a high-spreading oil component which imparts an almost instantaneous and relatively long-lasting feeling of smoothness to the skin and has good dermatological compatibility.

9 Claims, No Drawings

POLY-α-OLEFIN-CONTAINING COSMETIC COMPOSITION

CROSS REFERENCE TO RELATED APPLICATIONS

This is a continuation of U.S. application Ser. No. 10/553,182, which is the National Phase entry of PCT/EP2004/003699, filed Apr. 7, 2004, which claims priority to German application DE 103 17 781.7, filed Apr. 16, 2003, the contents of which are incorporated by reference in their entirety.

FIELD OF THE INVENTION

This invention relates to new cosmetic compositions containing certain poly-α-olefins and to the use of these poly-α-olefins as oil components in cosmetic and pharmaceutical preparations. The cosmetic or pharmaceutical preparations show good dermatological compatibility and impart a particularly light feeling on the skin.

BACKGROUND OF THE INVENTION

Consumers expect cosmetic skin- and hair-care emulsions to satisfy a range of requirements. Apart from the cleaning and skin-/hair-care effects which determine the intended application, value is placed on such diverse parameters as very high dermatological compatibility, good lipid-layer-enhancing properties, elegant appearance, optimal sensory impression and stability in storage.

Besides a number of surfactants, preparations used to clean and care for the human skin and hair contain, above all, oil components and water. The oil components/emollients used include, for example, hydrocarbons, ester oils and vegetable and animal oils/fats/waxes. In order to meet stringent commercial requirements in regard to sensory properties and optimal dermatological compatibility, new oil components and emulsifier mixtures are continually being developed and tested. A large number of natural and synthetic oils, for example almond or avocado oil, ester oils, ethers, alkyl carbonates, hydrocarbons and silicone oils, are used in the production of cosmetic or pharmaceutical preparations. A key function of the oil components—besides their care effect which is directly related to lipid layer enhancement of the skin—is to provide the skin of consumers with a non-sticky, almost instantaneous and long-lasting feeling of smoothness and suppleness.

The subjective feeling on the skin can be correlated and objectivized with the physicochemical parameters of the spreading of the oil components on the skin, as illustrated by U. Zeidler in the journal Fette, Seifen, Anstrichmittel 87, 403 (1985). According to this reference, cosmetic oil components can be classified as low-spreading ($<300$ mm$^2$/10 mins.), medium-spreading ($>/=300$ to 1000 mm$^2$/10 mins.) and high-spreading oils ($>/=1000$ mm$^2$/10 mins.). If a high-spreading oil is used as the oil component in a predetermined formulation, the required feeling of smoothness of the skin is achieved very quickly and, where cyclomethicones, for example Dow Corning 245 fluid (Dow Corning Corporation) or Abil® B 8839 (Goldschmidt Chemical Corporation), are used, a velvety feeling desirable to the consumer is also obtained. Unfortunately, the experience does not last long because the high volatility of the last-mentioned structures means that the pronounced feeling of smoothness and hence the velvety feel disappear very quickly, leaving the skin with an unpleasant, dull feeling.

However, cyclomethicones have the advantage over other hydrocarbon-based emollients, such as very light mineral oils, polybutylenes (for example Arlamol® HD, ICI), ethyl hexyl cyclohexane (Cetiol® S, Cognis Deutschland GmbH & Co. KG), that they have a very light feeling on the skin. Accordingly, there is a need for hydrocarbon-based oil components/emollients which combine the advantages of the cyclomethicones, such as a light feeling on the skin and good spreading properties, without having any of their disadvantages.

The problem addressed by the present invention was to provide improved, high-spreading oil components and preparations containing them which would impart an almost instantaneous and relatively long-lasting feeling of smoothness to the skin and which would show good dermatological compatibility. In addition, the oil components would lend themselves to simple and stable incorporation in emulsions, would be hydrolysis-stable in the event of pH variations and would lead to low-viscosity compositions imparting a very light feeling on the skin.

SUMMARY OF THE INVENTION

The present invention relates to a cosmetic composition containing at least one poly-α-olefin obtainable by subjecting at least one primary alcohol to dehydrating polymerization at 60 to 340° C. in the presence of acidic alumino layer silicate, the primary alcohol being selected from the group consisting of
a) unsaturated monofunctional alcohols,
b) branched monofunctional alcohols and
c) difunctional alcohols.

DETAILED DESCRIPTION OF THE INVENTION

The poly-α-olefins used in the cosmetic composition according to the invention have already been described. They are mentioned in applicants' German patent application DE 10152267 and in International patent application PCT/EP02/11392. Besides describing the compounds themselves, the documents in question also contain detailed information on their production. Reference is made here to the corresponding applications.

Purely by way of a brief summary, it is pointed out that the reaction of the primary alcohol is preferably carried out in an inert gas atmosphere with continuous removal of the water formed. The acidic alumino layer silicate used as catalyst preferably has an acid charge of 3 to 300 mval/100 g. Examples of alumino layer silicates are talcum and clays with a sheet structure, such as kaolinite, montmorillonite, bentonites and hectorites. It is appropriate to carry out the reaction with removal of water until no more water is eliminated. The reaction times are normally in the range from 2 to 48 hours. The catalyst is then removed, for example by filtration. The degree of oligomerization of the poly-α-olefins is in the range from 1 to 10. The adjustment of a particular degree of oligomerization can be achieved by returning the olefin entrained during the continuous removal of water to the reaction mixture, which leads to relatively high degrees of oligomerization. The poly-α-olefins obtained are odorless, colorless or yellowish products which may be liquid or solid. There is no exact structural formula for the poly-α-olefins obtained because, under the dehydrating polymerization conditions, the primary alcohols in question are isomerized into various unsaturated monomers which then polymerize with one another.

The primary alcohols mentioned may be used individually or in admixture with one another. Whereas the alkyl chain of the group b) alcohols is branched, the alkyl chains of the primary alcohols of groups a) and c) may be either linear or branched. The unsaturated alcohols may be mono- or poly-unsaturated, more particularly olefinically unsaturated.

Preferred cosmetic compositions are those in which the primary alcohol contains 6 to 72 carbon atoms and more particularly 6 to 24 carbon atoms.

The group a) alcohol is preferably a linear alcohol. Examples of unsaturated monofunctional alcohols of group a) are 10-undecen-1-ol, coleyl alcohol, elaidyl alcohol, ricinolyl alcohol, linoleyl alcohol, linolenyl alcohol, gadoleyl alcohol, erucyl alcohol and brassidyl alcohol.

The group b) alcohol is preferably an alcohol selected from the group of branched alcohols having b1) at least one methyl group and, more particularly, 1 to 6 methyl branches in the alkyl chain, b2) a $C_{2-18}$ branch in the alkyl chain and b3) a $C_{2-18}$ branch in the α-position to the terminal $CH_2OH$ group.

In the case of group b1) with at least one methyl branch in the alkyl chain, the methyl group may be positioned anywhere in the alkyl chain. Suitable examples are isooctyl alcohol, isononyl alcohol, isostearyl alcohol or isotridecyl alcohol. Of these, isononyl alcohol is particularly preferred. Where there are several methyl groups, they preferably number 2 to 6 in any distribution over the alkyl chain of the alcohol. In the case of group b2) alcohols branched by a $C_{2-18}$ alkyl group, there are preferably no other branches in the alkyl chain of the alcohol.

Other suitable primary monofunctional branched alcohols are the Guerbet alcohols known to the expert which are obtainable by dimerization of fatty alcohols and which, structurally, are distinguished by the presence of a relatively long alkyl chain, preferably with 2 to 18 carbon atoms, in the α-position to the terminal $CH_2OH$ group. Suitable Guerbet alcohols are 2-hexyl decanol, 2-butyl octanol, 2-octyl dodecanol and 2-hexyldecyl palmitate/stearate, 2-ethyl hexanol and 2-propyl heptanol. 2-Ethyl hexyl alcohol is preferred.

Suitable group c) alcohols, i.e. difunctional alcohols (with 2 hydroxyl groups), are saturated or unsaturated diols, such as pentane-1,5-diol, octane-1,8-diol, hexane-1,6-diol, decane-1,10-diol, dodecane-1,12-diol, octadecane-1,12-diol or the dimer diols known to the expert.

The poly-α-olefins may be used in unsaturated form in the cosmetic composition according to the invention. In the interests of greater oxidation stability, however, the poly-α-olefins are preferably hydrogenated after the dehydrating polymerization and used in the hydrogenated (hardened) form in the compositions according to the invention.

The hydrogenation is described in the above-cited International patent application PCT/EP02/11392 and may be carried out in known manner at temperatures in the range from 150° C. to 250° C. and preferably at temperatures in the range from 190 to 210° C. and under pressures of 20 to 150 bar (low-pressure process) or 150 to 350 bar (high-pressure process). Suitable catalysts are the hydrogenation catalysts known from the prior art, such as nickel or the noble metal catalysts, more particularly based on palladium or platinum. Particularly suitable noble metal catalysts are palladium catalysts, more particularly palladium on coal. The catalyst may be added to the poly-α-olefins in typical quantities either in the form of a suspension or in solid form. For the preferred palladium on coal, the quantities used are in the range from 0.001 to 5% by weight, expressed as palladium. However, the catalyst may also be applied to a solid carrier material, such as active charcoal, graphite, kieselguhr, silica gel, spinets, aluminium oxide or ceramic materials. Other suitable catalysts are nickel catalysts, for example suspended nickel, such as Nysofact 101 I a (Engelhard), which is preferably used in quantities of 0.01 to 5% by weight, based on nickel.

As already mentioned, the described poly-α-olefins are colorless to pale yellowish, substantially odorless compounds with high spreading values, typically above 1,000 $mm^2/10$ minutes and preferably above 1,600 $mm^2/10$ minutes (Zeidler's definition). Accordingly, they are eminently suitable for use as oil components in cosmetic or pharmaceutical preparations. Wherever poly-α-olefins in general are mentioned in the following, both the hydrogenated and the non-hydrogenated compounds are included.

Cosmetic Preparations

The compound according to the invention allows the production of stable cosmetic emulsions. These cosmetic emulsions are preferably body care formulations, for example in the form of creams, milks, lotions, sprayable emulsions, products for eliminating body odor, etc. The compound according to the invention may also be used in surfactant-containing formulations such as, for example, foam and shower baths, hair shampoos and care rinses.

The cosmetic preparations may be formulated as emulsions or dispersions which contain water and the oil phase alongside one another. Preferred cosmetic compositions are those in the form of a w/o or o/w emulsion with the usual concentrations—known to the expert—of oils/fats/waxes, emulsifiers, water and the other auxiliaries and additives typically used in cosmetic preparations.

The cosmetic composition according to the invention contains 1 to 50% by weight, preferably 5 to 40% by weight and more particularly 5 to 25% by weight oil of components which, together for example with oil-soluble surfactants/emulsifiers and oil-soluble active components, form part of the so-called oil or fatty phase. In the context of the invention, the oil components include fatty compounds, waxes and liquid oils, but not emulsifiers/surfactants. The poly-α-olefins may be present as sole oil component or in combination with other oils/fats/waxes. The percentage content of the at least one poly-α-olefin, based on the total quantity of oil components, is 0.1 to 100% by weight and preferably 1 to 50% by weight. Quantities of 1 to 20% by weight and more especially 3 to 20% by weight are particularly preferred.

Depending on the particular application envisaged, the cosmetic formulations contain a number of other auxiliaries and additives, such as, for example, surface-active substances (surfactants, emulsifiers), other oil components, pearlizing waxes, consistency factors, thickeners, superfatting agents, stabilizers, polymers, silicone compounds, fats, waxes, lecithins, phospholipids, biogenic agents, UV protection factors, antioxidants, deodorants, antiperspirants, antidandruff agents, film formers, swelling agents, insect repellents, self-tanning agents, tyrosinase inhibitors (depigmenting agents), hydrotropes, solubilizers, preservatives, perfume oils, dyes, etc. which are listed by way of example in the following.

The quantities of the particular additives are governed by the particular application envisaged. In another preferred embodiment, the cosmetic composition contains 0.1 to 20% by weight, preferably 1 to 15% by weight and more particularly 1 to 10% by weight of a surface-active substance or a mixture of surface-active substances.

Surface-Active Substances

The surface-active substances present may be anionic, nonionic, cationic and/or amphoteric or zwitterionic surfactants or emulsifiers or a mixture thereof. In surfactant-containing cosmetic preparations such as, for example, shower gels, foam baths, shampoos, etc., at least one anionic surfactant is preferably present. Body-care creams and lotions preferably contain nonionic surfactants/emulsifiers.

Typical examples of anionic surfactants are soaps, alkyl benzene-sulfonates, alkanesulfonates, olefin sulfonates, alkylether sulfonates, glycerol ether sulfates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, polyglycerol esters, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. Typical examples of amphoteric or zwitterionic surfactants are alkylbetaines, alkylamidobetaines, amino-propionates, aminoglycinates, imidazolinium betaines and sulfobetaines. The surfactants mentioned are all known compounds. Information on their structure and production can be found in relevant synoptic works in this field. Typical examples of particularly suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligo-glucosides, fatty acid glucamides, alkylamidobetaines, amphoacetals and/or protein fatty acid condensates, preferably based on wheat proteins.

Oil Components

Body care preparations, such as creams, lotions and milks, normally contain a number of other oil components and emollients which contribute towards further optimizing their sensory properties. Suitable oil components are, for example, Guerbet alcohols based on fatty alcohols containing 6 to 18 and preferably 8 to 10 carbon atoms, esters of linear $C_{6-22}$ fatty acids with linear or branched $C_{6-22}$ fatty alcohols or esters of branched $C_{6-13}$ carboxylic acids with linear or branched $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol and isopropanol, esters of $C_{18-38}$ alkylhydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, such as Dicaprylyl Carbonate (Cetiol® CC) for example, Guer-bet carbonates based on $C_{6-18}$ and preferably $C_{8-10}$ fatty alcohols, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, such as Dicaprylyl Ether (Cetiol® OE) for example, ring opening products of epoxidized fatty acid esters with polyols, silicone oils (cyclomethicone, silicon methicone types, etc.) and/or aliphatic or naphthenic hydrocarbons such as, for example, mineral oil, Vaseline, petrolatum, isohexadecanes, squalane, squalene or dialkyl cyclohexanes.

Fats and Waxes

Fats and waxes are added to the body care products both as care components and to increase the consistency of the cosmetic preparations. Typical examples of fats are glycerides, i.e. solid or liquid, vegetable or animal products which consist essentially of mixed glycerol esters of higher fatty acids. Fatty acid partial glycerides, i.e. technical mono- and/or di-esters of glycerol with $C_{12-18}$ fatty acids, such as for example glycerol mono/dilaurate, palmitate or stearate, may also be used for this purpose. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Thickeners

Suitable thickeners are, for example, Aerosil® types (hydrophilic silicas), polysaccharides, more especially xanthan gum, guar-guar, agar-agar, alginates and tyloses, carboxymethyl cellulose and hydroxyethyl and hydroxypropyl cellulose, polyacrylates (for example Carbopols® and Pemulen types [Goodrich]; Synthalens® [Sigma]; Keltrol types [Kelco]; Sepigel types [Seppic]; Salcare types [Allied Colloids]), polyacrylamides, polymers, polyvinyl alcohol and polyvinyl pyrrolidone. Other consistency factors which have proved to be particularly effective are bentonites, for example Bentone® Gel VS-5PC (Rheox) which is a mixture of cyclopentasiloxane, Disteardimonium Hectorite and propylene carbonate, and a sodium polyacrylate known as Cosmedia® SP. Other suitable consistency factors are electrolytes, such as sodium chloride and ammonium chloride.

Stabilizers

Metal salts of fatty acids such as, for example, magnesium, aluminium and/or zinc stearate or ricinoleate may be used as stabilizers.

UV Protection Factors and Antioxidants

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

- 3-benzylidene camphor or 3-benzylidene norcamphor and derivatives thereof, for example 3-(4-methylbenzylidene)-camphor;
- 4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;
- esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);
- esters of salicylic acid, preferably salicylic acid-2-ethylhexyl ester, salicylic acid-4-isopropylbenzyl ester, salicylic acid homomethyl ester;
- derivatives of benzophenone, preferably 2-hydroxy-4-methoxybenzophenone, 2-hydroxy-4-methoxy-4'-methylbenzophenone, 2,2'-dihydroxy-4-methoxybenzophenone;
- esters of benzalmalonic acid, preferably 4-methoxybenzalmalonic acid di-2-ethylhexyl ester;
- triazine derivatives such as, for example, 2,4,6-trianilino-(p-carbo-2'-ethyl-1'-hexyloxy)-1,3,5-triazine and Octyl Triazone or Dioctyl Butamido Triazone (Uvasorb® HEB);
- propane-1,3-diones such as, for example, 1-(4-tert.butylphenyl)-3-(4'-methoxyphenyl)-propane-1,3-dione;
- ketotricyclo(5.2.1.0)decane derivatives.

Suitable water-soluble substances are

- 2-phenylbenzimidazole-5-sulfonic acid and alkali metal, alkaline earth metal, ammonium, alkylammonium, alkanolammonium and glucammonium salts thereof and 2,2-(1,4-phenylene)-bis-1H-benzimidazole-4,6-disulfonic acid and salts thereof, more particularly the sodium salt;
- sulfonic acid derivatives of benzophenones, preferably 2-hydroxy-4-methoxybenzophenone-5-sulfonic acid and salts thereof;
- sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol® 1789) or 1-phenyl-3-(4'-isopropylphenyl)-propane-1,3-dione and enamine compounds. The UV-A and UV-B filters may of course also be used in the form of mixtures. Particularly favorable combinations consist of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide. Silicates (talcum), barium sulfate and zinc stearate may be used as salts. The oxides and salts are used in the form of the pigments for skin-care and skin-protecting emulsions.

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin.

Biogenic Agents

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prunus extract, bambara nut extract, and vitamin complexes.

Deodorants

Deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers.

Germ Inhibitors

Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxy-diphenylether (triclosan), 4-chloro-3,5-dimethylphenol, 2,2'-methylene-bis-(6-bromo-4-chlorophenol), 3-methyl-4-(1-methyl-ethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

Enzyme Inhibitors

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Odor Absorbers

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of ladanum or styrax or certain abietic acid derivatives as their principal component. Odor maskers are perfumes or perfume oils which, besides their odor-masking function, impart their particular perfume note to the deodorants.

Antiperspirants

Antiperspirants reduce perspiration and thus counteract underarm wetness and body odor by influencing the activity of the eccrine sweat glands.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine.

Antidandruff Agents

Suitable antidandruff agents are piroctone olamine (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Insect Repellents

Suitable insect repellents are N,N-diethyl-m-toluamide, pentane-1,2-diol or 3-(N-n-butyl-N-acetylamino)-propionic acid ethyl ester), which is marketed under the name of Insect Repellent® 3535 by Merck KGaA, and butyl acetylaminopropionate.

Self-Tanning Agents and Depigmenting Agents

A suitable self-tanning agent is dihydroxyacetone. Suitable tyrosine inhibitors which prevent the formation of melanin and are used in depigmenting agents are, for example, arbutin, ferulic acid, koji acid, coumaric acid and ascorbic acid (vitamin C).

Hydrotropes

In addition, hydrotropes, for example ethanol, isopropyl alcohol or polyols, may be used to improve flow behavior. Suitable polyols preferably contain 2 to 15 carbon atoms and at least two hydroxyl groups.

Preservatives

Suitable preservatives are, for example, phenoxyethanol, formal-dehyde solution, parabens, pentanediol or sorbic acid and the silver complexes known under the name of Surfacine® and the other classes of compounds listed in Appendix 6, Parts A and B of the Kosmetikverordnung ("Cosmetics Directive").

Perfume Oils and Aromas

Suitable perfume oils are mixtures of natural and synthetic perfumes. Natural perfumes include the extracts of blossoms, stems and leaves, fruits, fruit peel, roots, woods, herbs and grasses, needles and branches, resins and balsams. Animal raw materials, for example civet and beaver, and synthetic perfume compounds of the ester, ether, aldehyde, ketone, alcohol and hydrocarbon type may also be used.

Dyes

Suitable dyes are any of the substances suitable and approved for cosmetic purposes. Examples include cochineal red A (C.I. 16255), patent blue V (C.I. 42051), indigotin (C.I. 73015), chlorophyllin (C.I. 75810), quino-line yellow (C.I. 47005), titanium dioxide (C.I. 77891), indanthrene blue RS (C.I. 69800) and madder lake (C.I. 58000). These dyes are normally used in concentrations of 0.001 to 0.1% by weight, based on the mixture as a whole.

EXAMPLES

In the following Examples, AV stands for acid value, IV for iodine value and OHV for hydroxyl value.

Example 1

2,700 g isononyl alcohol were heated under nitrogen in the presence of 5% by weight of the catalyst K5 until the separation of water was observed. The reaction mixture was kept at that temperature until there was no further elimination of water. The still hot reaction mixture was removed from the catalyst by filtration and gave a clear colorless product. Analysis: AV=0.1, IV=167, OHV=0.7.

Example 2

1,200 g 2-ethyl hexanol were heated under nitrogen in the presence of 5% by weight of the catalyst K5 until the separation of water was observed. The reaction mixture was kept at that temperature until there was no further elimination of water. The still hot reaction mixture was removed from the catalyst by filtration and gave a clear, colorless product. Analysis: AV=0.2, IV=217, OHV=0.4.

Example 3

1,030 g poly-α-olefin based on isononyl alcohol (obtained from Example 1) and 0.05% by weight palladium on coal were treated with 100 bar hydrogen for 5 hours at 200° C. The catalyst was filtered off and the product deodorized. Analysis: OHV=0.9, AV=1.6, IV=0.1.

Example 4

560 g poly-α-olefin based on 2-ethylhexanol (obtained from Example 2) and 0.05% by weight palladium on coal were treated with 100 bar hydrogen for 5 hours at 200° C. The catalyst was filtered off and the product deodorized. Analysis: OHV=0.1, IV=1.1, AV=0.1.

Cosmetic Compositions

Example 5

The following o/w emulsion was prepared using the poly-α-olefin of Example 3 as oil component:

| | |
|---|---|
| Eumulgin ® B2 | 2% by weight |
| Lanette ® O | 5% by weight |
| Oil component | 16% by weight |
| Glycerol | 3% by weight |
| Water | 73.85% by weight |
| Formalin (37%) | 0.15% by weight |

Example 6

The following o/w emulsion was prepared using the poly-α-olefin of Example 3 as oil component:

| | |
|---|---|
| Eumulgin ® VL 75 | 4.5% by weight |
| Oil component | 16% by weight |
| Carbopol ® | 0.3% by weight |
| KOH (20%) | 0.7% by weight |
| Glycerol | 3% by weight |
| Water | 75.35% by weight |
| Formalin (37%) | 0.15% by weight |

Example 7

The following o/w emulsion was prepared using the poly-α-olefin of Example 3 as oil component:

| | |
|---|---|
| Dehymuls ® PGPH | 5% by weight |
| Oil component | 20% by weight |
| Glycerol | 5% by weight |
| Mg sulfate•7H$_2$O | 1% by weight |
| Water | 68.85% by weight |
| Formalin (37%) | 0.15% by weight |

The isononyl oligomer poly-α-olefin had a constant viscosity (ca. 5,000 mPas) over the storage period of 12 weeks at room temperature. The emulsions containing Carbopol® were stable over 4 weeks both at minus 5° C. and at 40, 45 and 50° C.

Table 1 below shows the viscosity and storage stability tests for the emulsion of Example 6 by comparison with emulsions containing Nexbase® 2006 FG or thinly liquid paraffin oil as the oil component. In contrast to the emulsion according to the invention, the comparison emulsions had separated after about 1 week under these conditions.

TABLE 1

| | Isononyl oligomer hydrogenated | Paraffin oil. thinly liquid | Nexbase ® 2006FG |
|---|---|---|---|
| Eumulgin ® VL 75 | 4.50 | 4.50 | 4.50 |
| Isononyl oligom. hydrogenated | 16.00 | — | — |
| Paraffin oil, thinly liquid | — | 16.00 | — |
| Nexbase ® 2006FG | — | — | 16.00 |
| Carbopol ® | 0.30 | 0.30 | 0.30 |
| KOH, 20% | 0.70 | 0.70 | 0.70 |
| Glycerol, 86% | 3.00 | 3.00 | 3.00 |
| Water, deionized | 75.35 | 75.35 | 75.35 |
| Formalin, 37% | 0.15 | 0.15 | 0.15 |
| Viscosity in mPas | | | |
| Day 1 | 4000 | 4800 | 4800 |
| 1 Weeks | 4000 | 6400 | 6000 |
| 4 Weeks | 4800 | — | — |
| 8 Weeks | 5200 | — | — |
| 12 Weeks | 4800 | — | — |
| Stabilities * | | | |
| 1 Week RT/−5° C./40° C./45° C./50° C. | 1/1/1/1 | 1/1/1/5/5 | 1/1/1/1 |
| 4 Weeks RT/−5° C./40° C./45° C./50° C. | 1/1/1/1 | 5/1/5/—/— | 5/5/5/5/5 |
| 8 Weeks RT/−5° C./40° C./45° C./50° C. | 1/1/1/1 | —/1/—/—/— | —/—/—/—/— |
| 12 Weeks RT/−5° C./40° C./45° C./50° C. | 1/1/1/1 | | —/—/—/—/— |

In Table 1, "1" = stable emulsion, "5" = non-stable emulsions and "—" = emulsions which were clearly unstable, i.e. had separated, RT = room temperature.

Examples of formulations which demonstrate the various potential applications of the cosmetic compositions according to the invention are presented in the following Tables. All quantities represent percentages by weight of the commercially available substances in the composition as a whole.

TABLE 2

| O/W sun protection emulsions | | | | | | | | | | | |
|---|---|---|---|---|---|---|---|---|---|---|---|
| Component | 1 | 2 | 3 | 4 | 5 | 6 | 7 | 8 | 9 | 10 | 11 |
| L = Lotion, C = Cream | L | C | S | L | C | L | L | C | L | C | L |
| Eumulgin ® VL 75 | | | | | | 4 | 4 | 2 | | | |
| Eumulgin ® B2 | 2 | | | | | | | | | | |
| Tween ® 60 | | | | 1 | | | | | | | |
| Myrj ® 51 | | 3 | | 2 | | | | | | | |
| Cutina ® E 24 | 1 | | | 1 | | | | | | | |
| Hostaphat ® KL 340 N | | | | | | | | | 2 | | |
| Lanette ® E | | | 0.5 | | | | | 0.5 | | | |
| Amphisol ® K | | | 1 | | | 1 | | 0.5 | | 1 | |
| Sodium stearate | | | | | | | 1 | | | | 2 |
| Emulgade ® PL 68/50 | | | | 1 | 5 | | | | | 4 | |
| Tego ® Care 450 | | | | | | | | | | 3 | |
| Cutina ® MD | 2 | | 6 | | 4 | | | | 6 | | |
| Lanette ® 14 | 1 | | 1 | | | | | 2 | | | 4 |

TABLE 2-continued

| Component | O/W sun protection emulsions | | | | | | | | | | |
|---|---|---|---|---|---|---|---|---|---|---|---|
| | 1 | 2 | 3 | 4 | 5 | 6 | 7 | 8 | 9 | 10 | 11 |
| Lanette ®O | 1 | 6 | | | 5 | 2 | | 2 | | | |
| Antaron V 216 | | | 1 | | 2 | 2 | | | | 1 | |
| Emery ® 1780 | | | | | 0.5 | 0.5 | | | | | |
| Lanolin, anhydrous, USP | | | | | | | 5 | | | | |
| Poly-α-olefin (Example 4) | 2 | 2 | 4 | 1 | 2 | 2 | 2 | 1 | 2 | 2 | 1 |
| Myritol ® PC | | | | | 5 | | | | | | |
| Myritol ® 331 | 5 | | 8 | | | 6 | | 10 | | 2 | |
| Finsolv ® TN | | | 1 | | | | | 1 | 8 | | |
| Cetiol ® CC | | 2 | 5 | | | 4 | 4 | 2 | | 2 | |
| Cetiol ® OE | | | 3 | | | | | | 2 | 3 | |
| Dow Corning DC ® 244 | 4 | | 1 | | 5 | | | 2 | | | 2 |
| Dow Corning DC ® 2502 | | 1 | | | 2 | | | | | | |
| Squatol ® S | | | | | | | 4 | | | | |
| Silikonöl Wacker AK ® 350 | | 2 | | | | | | | | | |
| Cetiol ® 868 | | | | | | 2 | | 4 | | | 7 |
| Cetiol ® J 600 | | | | | | 3 | 2 | | | 5 | |
| Mineral oil | | | | 9 | | | | | | | |
| Cetiol ® B | | | 1 | | | | | | | 2 | |
| Eutanol ® G | | | | | | | | | | | |
| Eutanol ® G 16 | | | | | | | | | | | |
| Cetiol ® PGL | | 5 | | | | | | | | 5 | |
| Almond oil | | | 2 | | | | 1 | | | | |
| Photonyl ® LS | | | | 2 | | | | | | 2 | |
| Panthenol | | | | | | 1 | | | | | |
| Bisabolol | | | | | | 0.2 | | | | | |
| Tocopherol/Tocopherylacetate | | | | | | 1 | | | | | |
| Photonyl ® LS | | | | | | | | | | | |
| Neo Heliopan ® Hydro (Na salt) | 2 | | 2.2 | | 3 | 3 | | | | | 2 |
| Neo Heliopan AP (Na salt) | 2 | | | | 1.5 | 2 | | 2 | 1 | | 1 |
| Neo Heliopan ® 303 | 3 | 5 | 9 | 4 | | | | | | | |
| Neo Heliopan ® BB | | | | | 1 | | | | | | 2 |
| Neo Heliopan ® MBC | 2 | | | 3 | | 2 | 2 | 2 | | | 1 |
| Neo Heliopan ® OS | | | | | | | | | | 10 | 7 |
| Neo Heliopan ® E 1000 | | 7.5 | | 6 | | | | | | | 6 |
| Neo Heliopan ® AV | | | 7.5 | | | 7.5 | 4 | 5 | | | |
| Uvinul ® T 150 | 2 | | | | 2.5 | | | 1 | | | |
| Parsol ® 1789 | | 1 | 1 | | | | 2 | | 2 | 2 | |
| Zinc oxide NDM | 10 | | 5 | | | 10 | | 3 | | 5 | 4 |
| Eusolex ® T 2000 | | | | | 5 | | 3 | 3 | | | 4 |
| Veegum ® Ultra | | | 0.7 | | | | | 1 | 1 | | |
| Keltrol ® T | | | 0.2 | | | | | 0.5 | 0.5 | | |
| Carbopol ® 980 | | 0.5 | | 0.2 | 0.2 | 0.2 | | 0.5 | 0.1 | 0.3 | 0.2 |
| Ethanol | | | | | | | | | | 10 | |
| Butylene glycol | | 2 | | 4 | 3 | | 2 | 5 | 2 | | 2 |
| Glycerin | 5 | 5 | 5 | | 3 | 3 | 2 | | 4 | | 3 |
| Preservative, NaOH Water | | | | | | q.s. to 100 | | | | | |

TABLE 3

| Component | O/W sun protection emulsions | | | | | | | | | | |
|---|---|---|---|---|---|---|---|---|---|---|---|
| | 12 | 13 | 14 | 15 | 16 | 17 | 18 | 19 | 20 | 21 | 22 |
| L = Lotion, C = Cream | L | L | L | C | L | C | S | C | C | L | L |
| Eumulgin ® VL 75 | 4 | 3 | 4.5 | | 3 | | | | 4 | | |
| Eumulgin ® B2 | | | | | | | | | | 1 | |
| Tween ® 60 | | | | | | | | | | 1 | |
| Myrj ® 51 | | | | | | | | | | | |
| Cutina ® E 24 | | | | | 2 | | | | | | |
| Hostaphat ® KL 340 N | | | | | | | | | | 0.5 | |
| Lanette ® E | 0.5 | | 0.5 | 0.5 | | | 0.1 | | 0.5 | | |
| Amphisol ® K | 0.5 | | | | | 1 | 1 | 1 | | | |
| Sodium stearate | | | | | 1 | | | | | | |
| Emulgade ® PL 68/50 | | 6 | | | | 4.5 | 1 | 5 | | | |
| Tego ® Care 450 | 1 | | | | | | | | 4 | | |
| Cutina ® MD | 1 | | | 8 | 6 | 1 | | | | 4 | 1 |
| Lanette ® 14 | | 2 | | | | | | 2 | | 1 | |
| Lanette ® O | | | | 2 | | | | | 1 | 2 | |
| Antaron V 220 | 1 | | | 2 | | | 0.5 | | | 2 | 0.5 |
| Poly-α-olefin (Example 4) | 4 | 2 | 4 | 6 | 10 | 4 | 2 | 8 | 2 | 1 | 3 |
| Myritol ® PC | | | | | | | | | 5 | | |
| Myritol ® 331 | 12 | | 12 | | 8 | 8 | | | | 10 | 8 |
| Finsolv ® TN | | | | | 5 | | | 3 | 3 | | |

TABLE 3-continued

O/W sun protection emulsions

| Component | 12 | 13 | 14 | 15 | 16 | 17 | 18 | 19 | 20 | 21 | 22 |
|---|---|---|---|---|---|---|---|---|---|---|---|
| Cetiol ® CC | 6 |  | 6 |  |  | 5 | 5 |  |  |  |  |
| Cetiol ® OE |  |  |  |  | 2 |  |  |  |  |  | 2 |
| Dow Corning DC ® 244 |  | 2 |  |  | 1 |  |  |  |  |  |  |
| Dow Corning DC ® 2502 |  | 1 |  |  | 1 |  |  |  |  |  |  |
| Ceraphyl ® 45 |  |  |  |  |  |  |  |  |  | 2 | 2 |
| Silikonöl Wacker AK ® 350 |  |  |  |  | 1 |  |  |  |  |  |  |
| Cetiol ® 868 |  | 2 |  |  |  |  |  |  |  |  |  |
| Cetiol ® J 600 |  | 2 |  |  |  |  |  |  |  |  |  |
| Mineral oil |  |  |  | 10 |  |  |  |  |  |  |  |
| Cetiol ® B | 4 |  | 4 |  |  |  |  | 4 |  |  |  |
| Eutanol ® G |  | 3 |  |  |  | 3 |  |  |  |  |  |
| Eutanol ® G 16 S | 10 |  |  |  |  |  |  |  |  |  |  |
| Cetiol ® PGL |  |  |  |  |  |  |  |  | 2 |  |  |
| Photonyl ® LS |  |  |  |  |  |  |  |  |  | 2 |  |
| Panthenol |  |  |  |  |  | 1 |  |  |  |  |  |
| Bisabolol |  |  |  |  |  | 0.2 |  |  |  |  |  |
| Tocopherol/Tocopherylacetate |  |  |  |  |  | 1 |  |  |  |  |  |
| Neo Heliopan ® Hydro (Na salt) |  |  |  |  |  |  |  |  |  | 3 |  |
| Neo Heliopan AP (Na salt) |  | 2 |  | 2 |  |  | 2 |  |  |  | 1 |
| Eusolex ® OCR | 6 |  | 9 |  | 5 | 7 | 9 |  | 4 |  | 7 |
| Neo Heliopan ® BB |  |  |  |  |  |  |  | 1 | 1 |  | 1 |
| Neo Heliopan ® MBC |  | 2 |  | 1 |  |  |  | 3 | 1 |  | 3 |
| Neo Heliopan ® OS | 2 |  |  |  |  |  |  |  | 7 |  |  |
| Neo Heliopan ® E1000 |  | 4 |  |  |  |  |  | 5 |  |  |  |
| Neo Heliopan ® AV |  | 4 | 7.5 | 5 |  |  |  | 5 | 4 | 7.5 |  |
| Uvinul ® T 150 | 1 |  |  |  |  |  |  |  | 1.3 | 1 | 1 |
| Parsol ® 1789 | 1 |  |  |  |  |  |  |  | 2 |  | 1 |
| Z-Cote ® HP 1 | 7 | 2 | 5 |  |  | 7 | 5 |  | 6 | 2 |  |
| Eusolex ® T 2000 | 5 | 2 |  |  | 10 |  | 10 |  |  | 2 |  |
| Veegum ® Ultra | 1.5 |  | 1.5 |  |  | 1.5 | 1.2 |  | 1 |  |  |
| Keltrol ® T | 0.5 |  | 0.5 |  |  | 0.5 | 0.4 |  | 0.5 |  |  |
| Pemulen ® TR 2 |  | 0.3 |  | 0.3 |  |  | 0.1 | 0.2 |  |  | 0.3 |
| Ethanol |  | 5 |  |  | 8 |  |  |  |  |  |  |
| Butylene glycol | 1 |  |  | 3 | 3 |  |  |  |  | 8 | 1 |
| Glycerin | 2 | 4 | 3 | 3 |  | 3 | 3 | 3 | 5 |  | 3 |
| Water/preservative/NaOH |  |  |  |  | to 100/q.s./q.s |  |  |  |  |  |  |

TABLE 4

W/O sun protection emulsions

| Component | 23 | 24 | 25 | 26 | 27 | 28 | 29 | 30 | 31 | 32 | 33 |
|---|---|---|---|---|---|---|---|---|---|---|---|
| L = Lotion; C = Cream | C | L | C | L | C | L | L | L | L | C | C |
| Dehymuls ® PGPH | 4 | 2 | 1 | 3 | 3 | 1 | 1 | 2 | 2 | 4 | 1 |
| Monomuls ® 90-O18 |  |  | 2 |  |  |  |  |  |  |  |  |
| Lameform ® TGI | 2 |  | 4 |  | 3 |  |  |  |  | 1 | 3 |
| Abil ® EM 90 |  |  |  |  |  |  | 4 |  |  |  |  |
| Glucate ® DO |  |  |  |  |  |  |  |  |  |  | 3 |
| Isolan ® PDI |  |  |  |  |  | 4 |  | 2 |  |  |  |
| Arlacel ® 83 |  |  |  | 2 |  |  |  |  |  |  |  |
| Elfacos ® ST9 |  |  |  |  |  |  |  |  | 2 |  |  |
| Elfacos ® ST37 |  |  |  |  |  |  |  |  |  |  |  |
| Arlacel ® P 135 |  |  | 2 |  |  |  |  |  |  |  |  |
| Dehymuls ® HRE 7 |  |  |  |  |  |  |  |  |  |  |  |
| Zinc stearate |  | 1 |  | 1 | 1 |  |  | 1 |  | 1 |  |
| Microcrystalline wax |  |  | 5 |  |  | 2 |  |  |  | 5 |  |
| Beeswax |  | 1 |  | 1 |  |  |  | 5 |  | 7 |  |
| Tego ® Care CG |  |  |  |  | 1 |  |  |  |  |  | .5 |
| Prisorine ® 3505 |  | 1 |  | 1 | 1 |  | 1 | 1 |  |  | 1 |
| Emery ® 1780 |  |  | 5 |  |  |  |  |  |  | 4 |  |
| Wool wax alcohol, anhydrous, USP |  |  |  |  |  |  |  |  |  |  | 1 |
| Antaron V 216 |  | 2 |  |  |  |  |  |  |  |  |  |
| Poly-α-olefin (Example 4) | 3 | 4 | 2 | 1 | 10 | 2 | 2 | 6 | 3 | 12 | 1 |
| Myritol ® PC |  |  |  |  | 3 |  | 4 |  |  |  |  |
| Myritol ® 331 | 10 |  |  |  | 3 | 6 |  |  |  | 8 |  |
| Finsolv ® TN |  |  |  | 5 |  |  | 5 |  |  |  |  |
| Cetiol ® CC | 12 | 22 |  |  |  | 2 |  | 2 |  | 5 |  |
| Cetiol ® OE |  |  |  |  | 4 |  | 5 | 4 | 2 |  |  |
| Dow Corning DC ® 244 |  |  |  |  |  |  | 2 |  |  |  |  |
| Dow Corning DC ® 2502 |  |  | 1 |  | 2 |  |  |  |  |  |  |
| Prisorine ® 3758 |  |  |  |  |  |  |  |  |  | 2 |  |
| Silikonöl Wacker AK ® 350 |  |  |  | 4 |  |  | 3 |  |  |  |  |

TABLE 4-continued

| W/O sun protection emulsions | | | | | | | | | | | |
|---|---|---|---|---|---|---|---|---|---|---|---|
| Component | 23 | 24 | 25 | 26 | 27 | 28 | 29 | 30 | 31 | 32 | 33 |
| Cetiol ® 868 | | | | | | | | | | 2 | |
| Eutanol ® G 16 | | 3 | | | | | | | | | |
| Eutanol ® G 16S | | | | | | | | | | | |
| Cetiol ® J 600 | | | 4 | | | 2 | | | | | |
| Ceraphyl ® 45 | | | | 2 | | | | 2 | | 6 | |
| Mineral oil | | | | | 4 | | | | | | |
| Cetiol ® B | | | 2 | 4 | | | | | | 3 | |
| Eutanol ® G | | | 3 | | | | | 8 | | | |
| Cetiol ® PGL | | 11 | | | | 4 | | | 9 | | |
| Almond oil | | | | | 1 | | 5 | | | | |
| Photonyl ® LS | | 2 | 1 | | | | | | 4 | | |
| Panthenol | | | | | | 1.0 | | | | | |
| Bisabolol | | | | | | 0.2 | | | | | |
| Tocopherol/Tocopherylacetate | | | | | | 1.0 | | | | | |
| Magnesium sulfate x 7 water | 1 | | | | | | | | | | |
| Neo Heliopan ® Hydro (Na salt) | | 2 | 3 | | | | | 2 | | | |
| Neo Heliopan AP (Na salt) | 2 | 1 | | | 2 | | | 1 | 2 | | 1 |
| Neo Heliopan ® 303 | | | | | 4 | | | | | 6 | |
| Neo Heliopan ® BB | | 4 | 2 | | | | 2 | | | | |
| Neo Heliopan ® MBC | | | | | | | | 4 | 3 | | |
| Neo Heliopan ® OS | | | | | | | | | | | |
| Neo Heliopan ® E 1000 | | | | | | | | | 5 | | |
| Neo Heliopan ® AV | | 3 | 6 | 6 | | 7.5 | 7.5 | | 5 | | 7.5 |
| Uvinul ® T 150 | | | | | 2.5 | | | 1 | 2 | | |
| Parsol ® 1789 | | 2 | | | | | | 1 | 2 | | |
| Zinc oxide NDM | | | | | | 6 | | | | | |
| Eusolex ® T 2000 | 15 | | 10 | | 5 | | 4 | | | | 4 |
| Ethanol | | | | | | | | | | 8 | |
| Butylene glycol | | | 2 | 6 | | | 2 | 5 | | | 2 |
| Glycerin | 5 | 3 | 3 | | 5 | 3 | 2 | | 10 | 4 | |
| Water, preservative | to 100, q.s. | | | | | | | | | | |

TABLE 5

| W/O sun protection emulsions | | | | | | | | | | | |
|---|---|---|---|---|---|---|---|---|---|---|---|
| Component | 34 | 35 | 36 | 37 | 38 | 39 | 40 | 41 | 42 | 43 | 44 |
| L = Lotion; C = Cream | L | C | L | L | C | L | L | L | L | C | C |
| Dehymuls ® PGPH | 3 | 1 | 5 | 1 | 1 | 3 | 2 | 4 | 0.5 | 1 | 4 |
| Monomuls ® 90-O18 | | 1 | | | | | | | | | |
| Lameform ® TGI | | | | | 4 | | | 1 | | 3 | 1 |
| Abil ® EM 90 | | | | 1 | | | | | | 2 | |
| Glucate ® DO | | | | | 3 | | | | 2 | | |
| Isolan ® PDI | | 3 | | | | | 4 | | | | |
| Arlacel ® 83 | | | | | | 3 | | | | | |
| Elfacos ® ST9 | | | | | | | | | | | 2 |
| Elfacos ® ST37 | 2 | | | | | | | | | | |
| Arlacel ® P 135 | | | | | | 3 | | | | | |
| Dehymuls ® HRE 7 | | | | | | | | | 4 | | |
| Zinc stearate | | 2 | 2 | 1 | 1 | | | 1 | 1 | | |
| Microcrystalline wax | | | | | 4 | | 1 | | | 4 | |
| Beeswax | | 4 | | 2 | | | 1 | | 2 | | 1 |
| Tego ® Care CG | | | | | | | | | | | |
| Isostearic acid | 1 | 1 | | | | | 1 | 1 | | 1 | 1 |
| Emery ® 1780 | | 7 | 3 | | | | | | | | |
| Wool wax alcohol, anhydrous, USP | | | | | | | | | | | |
| Antaron V 220 | | 0.5 | 2 | 1 | 1 | 1 | | | | | |
| Poly-α-olefin (Example 4) | 2 | 4 | 3 | 3 | 2 | 2 | 1 | 3 | 3 | 1 | 4 |
| Myritol ® PC | | | | | | | | | | | |
| Myritol ® 331 | 4 | 2 | 3 | | 5 | | | 8 | 5 | 4 | |
| Finsolv ® TN | | 5 | 5 | | | 7 | | | | | |
| Cetiol ® CC | 3 | 1 | | | | | 3 | 16 | | | 12 |
| Cetiol ® OE | | 3 | | 2 | | | 3 | | | | |
| Dow Corning DC ® 244 | | 4 | | 2 | | | | | | | |
| Dow Corning DC ® 2502 | | | | 1 | | | | | | | |
| Prisorine ® 3578 | | 1 | | | | | | | | | |
| Silikonöl Wacker AK ® 350 | | | | 1 | | | | | | | |
| Cetiol ® 868 | | | | | | | | | | | |
| Eutanol ® G 16 | | | | | | | | | | | 3 |
| Eutanol ® G 16S | | | | | | | | | | | 7 |
| Cetiol ® J 600 | | | | 3 | | | | | | | |
| Ceraphyl ® 45 | | | | 1 | | | | | | 5 | 4 |

TABLE 5-continued

| W/O sun protection emulsions | | | | | | | | | | | |
|---|---|---|---|---|---|---|---|---|---|---|---|
| Component | 34 | 35 | 36 | 37 | 38 | 39 | 40 | 41 | 42 | 43 | 44 |
| Mineral oil | | | | | | | 9 | | | | |
| Cetiol ® B | | | | | 3 | 3 | | | 2 | 2 | |
| Eutanol ® G | | | | 2 | | | | | | 5 | |
| Cetiol ® PGL | | | | | | | | | 2 | | |
| Almond oil | | | 2 | | | | | | | | |
| Photonyl ® LS | | | | | | | 3 | | | | 2 |
| Panthenol | | | | | | 1.0 | | | | | |
| Bisabolol | | | | | | 0.2 | | | | | |
| Tocopherol/Tocopherylacetate | | | | | | 1.0 | | | | | |
| Magnesium sulfate x 7 water | | | | | | 1 | | | | | |
| Neo Heliopan ® Hydro (Na salt) | | 4 | | | | | | 4 | | | |
| Neo Heliopan AP (Na salt) | 2 | | | 1 | 2 | | 1 | | | | |
| Neo Heliopan ® 303 | 6 | 2 | | | | | | | | 6 | |
| Neo Heliopan ® BB | | 2 | | 2 | | 2 | | | | | |
| Neo Heliopan ® MBC | 2 | | | | 3 | | 4 | | 2 | | |
| Neo Heliopan ® OS | | | | | 10 | | 8 | | | | |
| Neo Heliopan ® E 1000 | | | 5 | 6 | | | | | | 5 | |
| Neo Heliopan ® AV | | 5 | 5 | | | 7.5 | | | | 5 | |
| Uvinul ® T 150 | 1 | | | | 2 | 2 | | | 3 | 2 | |
| Parsol ® 1789 | | 1 | 1 | | | | 1 | | 0.5 | | |
| Z-Cote ® HP 1 | 4 | 10 | | | | | | 5 | | | 5 |
| Titanium dioxide T 805 | | | | 2 | | 3 | | 7 | | 4 | 7 |
| Ethanol | | | | | 8 | 10 | | | | | |
| Butylene glycol | 5 | 1 | | | 3 | 3 | | | 8 | 2 | |
| Glycerin | | | 6 | 2 | | | 5 | 5 | | 3 | 5 |
| Water, preservative | | | | | to 100, q.s. | | | | | | |

TABLE 6

| W/O care emulsions | | | | | | | | | | | |
|---|---|---|---|---|---|---|---|---|---|---|---|
| Component | 45 | 46 | 47 | 48 | 49 | 50 | 51 | 52 | 53 | 54 | 55 |
| L = Lotion, C = Cream | C | L | C | L | C | L | L | L | C | C | C |
| Dehymuls ® PGPH | 1 | 3 | 1 | 2 | 3 | 1 | 1 | 2 | 1 | 1 | 1 |
| Monomuls ® 90-O18 | 2 | | | | | | | | 2 | | 2 |
| Lameform ® TGI | 4 | 1 | | | 3 | | | 1 | 4 | 3 | 3 |
| Abil ® EM 90 | | | | | | 4 | | | | | |
| Isolan ® PDI | | | | | 4 | | | | | | |
| Glucate ® DO | | | | 5 | | | | | | | |
| Arlacel ® 83 | | | 5 | | | | | | | | |
| Dehymuls ® FCE | | | | | | | | | | | |
| Dehymuls ® HRE 7 | | | | | | | | 4 | | 1 | |
| Zinc stearate | 2 | 1 | | 1 | 1 | | | 1 | 1 | 1 | |
| Microcrystalline wax | | | 5 | | | 2 | | | | | 5 |
| Beeswax | 4 | | | 1 | | | | 1 | 4 | 7 | |
| Tego Care ® CG | | | | | 1 | | | | | | 0.5 |
| Prisorine ® 3505 | | | 1 | 1 | | 1 | 1 | | | 1 | |
| Dry Flo ® Plus | | | | | | | | | | | |
| SFE 839 | | | | | | | 3 | | | | |
| Emery ® 1780 | 1 | | | | | | | | | | 1 |
| Lanolin; anhydrous USP | | | 5 | | | | | | | 4 | |
| Poly-α-olefin (Example 4) | 3 | 4 | 2 | 12 | 10 | 2 | 2 | 6 | 3 | 12 | 1 |
| Cegesoft ® C 17 | | | 3 | | | | | | | 1 | |
| Myritol ® PC | | | | | | 2 | 4 | | | | |
| Myritol ® 331 | 6 | | | | 2 | 6 | 2 | | | 8 | |
| Finsolv ® TN | | | | 5 | | 2 | 5 | | | | |
| Cetiol ® A | | 6 | | | 4 | | | | | | |
| Cetiol ® CC | | 8 | | | 2 | 2 | 2 | | | 5 | |
| Cetiol ® SN | | 5 | | | | | | 3 | | | |
| Cetiol ® OE | 3 | | | | 4 | | 2 | | 4 | 2 | |
| Dow Corning DC ® 244 | | | | | 1 | | 2 | | | | |
| Dow Corning DC ® 2502 | | | 1 | | 2 | | | | | | |
| Prisorine ® 3758 | | | | | 3 | | | | | | |
| Silikonöl Wacker AK ® 350 | | | | 4 | | | | 3 | | | |
| Cetiol ® 868 | | | | | | | | | | 2 | 7 |
| Cetiol ® J 600 | | | 4 | | | 2 | | | | | |
| Ceraphyl ® 45 | | | | 2 | | | | 2 | | 6 | |
| Mineral oil | | | | | 4 | | | | | | |
| Cetiol ® B | | | 2 | 4 | | | | | | 3 | |
| Eutanol ® G 16 | | 1 | | | | | | | | 3 | |
| Eutanol ® G | | | 3 | | | | | 8 | | | |
| Cetiol ® PGL | | | | | | 4 | | | 9 | | |

TABLE 6-continued

W/O care emulsions

| Component | 45 | 46 | 47 | 48 | 49 | 50 | 51 | 52 | 53 | 54 | 55 |
|---|---|---|---|---|---|---|---|---|---|---|---|
| Almond oil | | | | | 1 | | | 5 | | | |
| Insect Repellent ® 3535 | 2 | | | | | | | | | | |
| N,N-Diethyl-m-toluamide | | | | 3 | | | | | 5 | | |
| Photonyl ® LS | 2 | 2 | | | | | | | | | |
| Panthenol | | | | | | 1.0 | | | | | |
| Bisabolol | | | | | | 0.2 | | | | | |
| Tocopherol/Tocopheryl Acetate | | | | | | 1.0 | | | | | |
| Magnesium sulfate x 7 water | | | | | | 1 | | | | | |
| Bentone ® 38 | | | | | 1 | | | | | | |
| Propylene carbonate | | | | | 0.5 | | | | | | |
| Ethanol | | | | | | | | | | 8 | |
| Butylene Glycol | | | 2 | 6 | | | | 2 | 5 | | 2 |
| Glycerin | 5 | 3 | 3 | | 5 | 3 | 2 | | | 10 | 4 |
| Water, preservative | | | | | to 100, q.s. | | | | | | |

TABLE 7

W/O care emulsions

| Component | 56 | 57 | 58 | 59 | 60 | 61 | 62 | 63 | 64 | 65 | 66 |
|---|---|---|---|---|---|---|---|---|---|---|---|
| L = Lotion, C = Cream | L | C | L | L | C | L | L | L | L | C | C |
| Dehymuls ® PGPH | 3 | 1 | 5 | 1 | 1 | 3 | 3 | 4 | 1 | 1 | 1 |
| Monomuls ® 90-O18 | | 1 | | 1 | | | | | | | |
| Lameform ® TGI | | | | | 4 | | | 1 | | 3 | |
| Abil ® EM 90 | | | | 3 | | | | | | 2 | |
| Isolan ® PDI | | 3 | | | | | | | | | 4 |
| Glucate ® DO | 1 | | | | | | | | | | |
| Arlacel ® 83 | | | | | | 3 | | | | | |
| Dehymuls ® FCE | | | | | 4 | | 1 | | | | |
| Dehymuls ® HRE 7 | | | | | | | | | 7 | | |
| Zinc stearate | | 2 | 2 | 1 | 1 | 1 | | 1 | 1 | | 1 |
| Microcrystalline wax | | | | | 4 | | 1 | | | 4 | |
| Beeswax | | 4 | | 2 | | 2 | 1 | 1 | 2 | | 5 |
| Tego ® Care CG | | | | | | | | | | | |
| Prisorine ® 3505 | 1 | 1 | | | | | 1 | 1 | | 1 | 1 |
| Dry Flo ® Plus | 1 | | | | | | | | | | |
| SFE ® 839 | | 5 | | | | 4 | | | | | |
| Emery ® 1780 | | | | | | | | | | | |
| Lanolin anhydrous USP | | 7 | 3 | | | | | | | | |
| Poly-α-olefin (Example 4) | 3 | 4 | 4 | 8 | 10 | 2 | 8 | 6 | 3 | 12 | 7 |
| Cegesoft ® C 17 | | | 2 | | | | | | | | |
| Myritol ® PC | | | | 8 | | | | | | | |
| Myritol ® 331 | 4 | | 3 | | 5 | 3 | | | 5 | 4 | |
| Finsolv ® TN | | | 5 | | | 7 | | | | | |
| Cetiol ® A | | | | | | | | 6 | | | |
| Cetiol ® CC | 3 | | | 6 | | 3 | 3 | | | 8 | |
| Cetiol ® SN | | | | | 5 | | | | | | |
| Cetiol ® OE | | 3 | | 2 | | | 3 | | | | 8 |
| Dow Corning ® DC 244 | | 4 | | 2 | | 2 | | | | | |
| Dow Corning ® DC 2502 | | | | 1 | | | | | | | |
| Prisorine ® 3758 | | | | | | 1 | | | | | |
| Silikonöl Wacker AK ® 350 | | | | 1 | | 1 | | 4 | | | |
| Cetiol ® 868 | | | | | | | | | | | 10 |
| Cetiol ® J 600 | 4 | | | 3 | | | | | | | |
| Ceraphyl ® 45 | | | | 1 | | | | | | 5 | 4 |
| Mineral oil | | | | | | | 9 | | | | |
| Cetiol ® B | | | | | 3 | 3 | | | 2 | 2 | |
| Eutanol ® G 16 | 1 | | | | | | | | | | |
| Eutanol ® G | | | | 2 | | | | | 5 | | |
| Cetiol ® PGL | | | 10 | | | | | 6 | | | 3 |
| Almond oil | | | 2 | | 5 | | 2 | | | | |
| Photonyl ® LS | | | | 2 | | | | | | | 2 |
| Panthenol | | | | | | 1.0 | | | | | |
| Bisabolol | | | | | | 0.2 | | | | | |
| Tocopherol/Tocopherylacetate | | | | | | 1.0 | | | | | |
| Magnesium sulfate x 7 water | | | | | | 1 | | | | | |
| Bentone ® 38 | | | | | | 1 | | | | | |
| Propylene carbonate | | | | | | 0.5 | | | | | |
| Ethanol | | | | | 8 | 10 | | | | | |
| Butylene glycol | 5 | 1 | | 3 | 3 | | | | 8 | 2 | 1 |
| Glycerin | | | 6 | 2 | | | 5 | 5 | | 3 | 5 |
| Water, preservative | | | | | to 100, q.s. | | | | | | |

TABLE 8

O/W care emulsions

| Component | 67 | 68 | 69 | 70 | 71 | 72 | 73 | 74 | 75 | 76 | 77 |
|---|---|---|---|---|---|---|---|---|---|---|---|
| L = Lotion, C = Cream | C | C | C | L | C | L | L | C | L | C | C |
| Eumulgin ® VL 75 | | | | | | 4 | | | | | |
| Dehymuls ® PGPH | | 2 | | | | | | | | | |
| Generol ® R | | | 1 | | | | | | | | |
| Eumulgin ® B2 | | | 0.8 | | | | | | | | |
| Tween ® 60 | | | | 1 | | | | | | | |
| Cutina ® E 24 | | | 0.6 | 2 | | | | | | | |
| Hostaphat ® KL 340 N | | | | | | | | | 2 | | |
| Lanette ® E | | | | | | | 1 | | | | |
| Amphisol ® K | | 0.5 | | | | 1 | | | | 1 | 0.5 |
| Sodium stearate | | | | | 0.5 | | | | | | |
| Emulgade ® PL 68/50 | | 2.5 | | | | | | | | 4 | |
| Tego ® Care CG | | | | | | | | | | | 2 |
| Tego ® Care 450 | | | | | | | | 5 | | | |
| Cutina ® MD | | 1 | | 6 | 5 | | 4 | | | 6 | |
| Lanette ® 14 | | | | 1 | | | | 2 | | | 4 |
| Lanette ® O | 4.5 | | 4 | | 1 | 2 | | | | | 2 |
| Novata ® AB | | 1 | | | | | | | | | 1 |
| Emery ® 1780 | | | | | 0.5 | 0.5 | | | | | |
| Lanolin, anhydrous, USP | | | | | | | 5 | | | | |
| Cetiol ® SB 45 | | | 1.5 | | | | 2 | | | | |
| Poly-α-olefin (Example 4) | 3 | 4 | 2 | 1 | 10 | 2 | 2 | 6 | 3 | 12 | 1 |
| Cegesoft ® C 17 | | | | | | | | | | | |
| Myritol ® PC | | | | | 5 | | | | | | |
| Myritol ® 331 | 2 | 5 | 5 | | | 6 | | 12 | | | |
| Finsolv ® TN | | | 2 | | | 2 | | | 8 | | |
| Cetiol ® CC | 4 | 6 | | | | 4 | 4 | | | | 5 |
| Cetiol ® OE | | | | | | | | | 4 | 3 | |
| Dow Corning DC ® 245 | | | 2 | | 5 | 1 | | | | | |
| Dow Corning DC ® 2502 | | | | | 2 | 1 | | | | | |
| Prisorine ® 3758 | | | | | | 1 | | | | | |
| Silikonöl Wacker AK ® 350 | 0.5 | 0.5 | 0.5 | | | 1 | 4 | | | | |
| Cetiol ® 868 | | | | | 2 | | 4 | | | | |
| Cetiol ® J 600 | 2 | | 3 | | 3 | 2 | | | | 5 | |
| Ceraphyl ® 45 | | | | | | | 3 | | | | |
| Mineral oil | | | | 9 | | | | | | | |
| Cetiol ® SN | | | 5 | | | | | | | | |
| Cetiol ® B | | | | | | | | | | 2 | |
| Eutanol ® G | | 2 | | 3 | | | | | | | |
| Cetiol ® PGL | | | | | | | | | 5 | 5 | |
| Dry Flo ® Plus | 5 | | | | | | 1 | | | | |
| SFE 839 | 5 | | | | | | | | | | 2 |
| Almond oil | | | | | | | 1 | | | | |
| Insect Repellent ® 3535 | | 2 | 4 | | | 2 | | | | 3 | |
| N,N-Diethyl-m-toluamide | | 2 | | | | | | | | 3 | |
| Photonyl ® LS | 2 | 2 | | | | 2 | | | | | |
| Panthenol | | | | | | 1 | | | | | |
| Bisabolol | | | | | | 0.2 | | | | | |
| Tocopherol/Tocopherylacetate | | | | | | 1 | | | | | |
| Veegum ® ultra | | | | | | | | | 1 | | |
| Keltrol ® T | | | 0.4 | | | | | | 0.5 | | |
| Pemulen ® TR 2 | 0.3 | | | | | | | 0.3 | | | |
| Carbopol ® Ultrez 10 | | 0.3 | 0.3 | 0.2 | 0.2 | 0.2 | | | 0.1 | 0.3 | 0.2 |
| Ethanol | | | | | | | | | | 10 | |
| Butylene glycol | | | | 4 | 3 | | | 2 | 5 | 2 | |
| Glycerin | 2 | 5 | 5 | | 3 | 3 | | 2 | | 4 | 3 |
| Water, preservative, NaOH | to 100, q.s., pH 6.5-7.5 ||||||||||||

TABLE 9

O/W care emulsions

| Component | 78 | 79 | 80 | 81 | 82 | 83 | 84 | 85 | 86 | 87 | 88 |
|---|---|---|---|---|---|---|---|---|---|---|---|
| L = Lotion, C = Cream | C | C | L | C | L | C | L | L | L | L | C |
| Eumulgin ® VL 75 | 4 | 3 | | | | | 1 | | | 2 | |
| Generol ® R | | | | | 2 | | | | | | |
| Eumulgin ® B2 | | | | | 2 | | | | 1 | | |
| Tween ® 60 | | | | | | | | 1 | | | |
| Cutina ® E 24 | | | 2 | | | | | | | | |
| Hostaphat ® KL 340 N | | | | | | | | | | | |
| Lanette ® E | 0.5 | | | | | | | | | | 1 |
| Amphisol ® K | 0.5 | 1 | | | | | 1 | 1 | | | |

TABLE 9-continued

O/W care emulsions

| Component | 78 | 79 | 80 | 81 | 82 | 83 | 84 | 85 | 86 | 87 | 88 |
|---|---|---|---|---|---|---|---|---|---|---|---|
| Sodium stearate | | | | | 1 | | | | | | |
| Emulgade ® PL 68/50 | | 6 | | | | | | 5 | | 4 | |
| Tego ® Care CG | | | | | | | | | | | |
| Tego ® Care 450 | | | | | | | | | 4 | | |
| Cutina ® MD | 3 | | 3 | 8 | | 6 | 8 | | | 4 | |
| Lanette ® 14 | | 2 | | | | | | 2 | | 1 | |
| Lanette ® O | 2 | | | 2 | | 3 | 1 | | 1 | 1 | 6 |
| Novata ® AB | | | | | | | | | | | |
| Emery ® 1780 | | | | | | | | | | | |
| Lanolin, anhydrous, USP | | | | | | 4 | | | | | |
| Cetiol ® SB 45 | | | | | | | 2 | | | | |
| Poly-α-olefin (Example 4) | 3 | 4 | 2 | 1 | 10 | 2 | 2 | 6 | 3 | 12 | 1 |
| Cegesoft ® C 17 | 4 | | | | | | | | | | |
| Myritol ® PC | 6 | | | | | 5 | | | 5 | | |
| Myritol ® 331 | 5 | | 5 | | | | 7 | | | 10 | 3 |
| Finsolv ® TN | | 5 | | | 5 | | | 3 | 3 | | 1 |
| Cetiol ® CC | | | | | | | | | | | 2 |
| Cetiol ® OE | | | | | 2 | | 2 | | 5 | | |
| Dow Corning DC ® 245 | | 2 | | | 1 | | | | | 8 | 2 |
| Dow Corning DC ® 2502 | | 1 | | | 1 | | | | | | 3 |
| Prisorine ® 3758 | 3 | | | | | | | | | | 2 |
| Silikonöl Wacker AK ® 350 | | | | | 1 | | | | | | 1 |
| Cetiol ® 868 | | 2 | | | | | | | | | |
| Cetiol ® J 600 | | 2 | | | | | | | | | |
| Ceraphyl ® 45 | | | | | | | | 3 | | | |
| Cetiol ® SN | | | | | | | | | | | |
| Cetiol ® B | | | 5 | | | 5 | | 4 | | | 3 |
| Eutanol ® G | | 3 | 5 | | 5 | | | | | | |
| Cetiol ® PGL | | | | | | | | | 5 | 2 | |
| Dry Flo ® Plus | | 1 | | | | | | | | | 1 |
| SFE 839 | 1 | 1 | | | | | | | | | |
| Almond oil | | | | | | 2 | | | | | |
| Photonyl ® LS | | | | | | 2 | | | | | |
| Panthenol | | | | | | 1 | | | | | |
| Bisabolol | | | | | | 0.2 | | | | | |
| Tocopherol/Tocopherylacetate | | | | | | 1 | | | | | |
| Veegum ® Ultra | | | | | | | | | 1 | | |
| Keltrol ® T | | | | | | | | | 0.5 | | |
| Carbopol ® ETD 2001 | | 0.3 | | 0.3 | | 0.5 | 0.2 | 0.2 | | | |
| Pemulen ® TR 2 | | | 0.3 | | | 0.3 | | | | | 0.5 |
| Ethanol | | 5 | | 8 | | | | | | 10 | |
| Butylene glycol | 5 | | 2 | 3 | 3 | | | | | 8 | |
| Glycerin | 2 | 4 | 3 | 3 | | 7 | 5 | 3 | 5 | | |
| Water, preservative, NaOH | | | | to 100, q.s. (pH 6.5-7.5) | | | | | | | |

TABLE 10

Spray formulations

| Component | 89 | 90 | 91 | 92 | 93 | 94 | 95 | 96 | 97 | 98 | 99 |
|---|---|---|---|---|---|---|---|---|---|---|---|
| S = Body spray, S* = Sun protection spray | S | S | S | S | S | S* | S* | S* | S* | S* | S* |
| Emulgade ® SE-PF | 8.9 | | 7.5 | 7.5 | 4.3 | 9.8 | 8.2 | 9.9 | | | |
| Eumulgin ® B2 | 3.1 | | 3 | | | | | 4.2 | | | |
| Eumulgin ® B3 | | | | | | 4.2 | 3.3 | | | | |
| Eumulgin ® HRE 40 | | | | | 4.7 | | | | | | |
| Cutina ® E 24 | | 5.9 | | 4 | | | | | | | |
| Amphisol ® K | | | | | | | | | 1 | 1 | 1 |
| Eumulgin ® VL 75 | | | | | | | | | | | 2 |
| Emulgade ® PL 68/50 | | 0.5 | | | | | | | 2.5 | 1 | |
| Cutina ® MD | | 3.1 | | | | | | | | | |
| Antaron V 220 | | | | | | 1 | 1 | 1 | | 1 | 1 |
| Poly-α-olefin (Example 4) | 11 | 5 | 7 | 7 | 7 | 5 | 4 | 5 | 5 | 4 | 6 |
| Myritol ® PC | | | | | | | | | | | |
| Myritol ® 331 | | | 3 | 4 | 3 | 3 | 3 | 3 | | | |
| Finsolv ® TN | | 4 | | | | | | 8 | | | |
| Cetiol ® CC | 6 | | | 5 | 5 | 2 | 2 | 4 | | | |
| Cetiol ® OE | | | 5 | 5 | | | 2 | | | | |
| Dow Corning DC ® 244 | | | 4 | 4 | 5 | | | | | | |
| Cetiol ® 868 | | 3 | | | | | | | | | |
| Cetiol ® J 600 | | | | 2 | 2 | | | | | | |
| Mineral oil | | | | 2 | | | | | | | |

TABLE 10-continued

| Spray formulations | | | | | | | | | | | |
|---|---|---|---|---|---|---|---|---|---|---|---|
| Component | 89 | 90 | 91 | 92 | 93 | 94 | 95 | 96 | 97 | 98 | 99 |
| Cetiol ® B | | | | | | | 2 | | | | |
| Eutanol ® G | 2 | | | 1 | | | | | | | |
| Photonyl ® LS | 2 | | | | | | 2 | | | 2 | 2 |
| Panthenol | | | | | 1 | | | | | | |
| Bisabolol | | | | | 0.2 | | | | | | |
| Tocopherol/Tocopherylacetate | | | | | 1 | | | | | | |
| Neo Heliopan ® Hydro (Na salt) | | | | | | 2 | | | | 3 | |
| Neo Heliopan AP (Na salt) | | | | | | 2 | 2 | 2 | | | 1 |
| Eusolex ® OCR | | | | | | | 2 | | | | 3 |
| Neo Heliopan ® BB | | | | | | | | | | 1 | |
| Neo Heliopan ® MBC | | | | | | 2 | 2 | 2 | | 1 | 1 |
| Neo Heliopan ® OS | | | | | | 5 | | | | | |
| Neo Heliopan ® AV | | | | | | 6 | 6 | 2 | | 7.5 | 2 |
| Uvinul ® T 150 | | | | | | 1 | 1 | 1 | | 1 | |
| Parsol ® 1789 | | | | | | 1 | | 1 | | 1 | |
| Z-Cote ® HP 1 | | | | | | | | | | 2 | 2 |
| Eusolex ® T 2000 | | | | | | | | | | 2 | 2 |
| Veegum ® Ultra | | | | | | | | | | | 1.5 |
| Laponite ®XLG | | | | | | | | | 1.5 | | |
| Keltrol ® T | | | | | | | | | | | 0.5 |
| Pemulen ® TR 2 | | | | | | | | | 0.2 | | |
| Insect Repellent ® 3535 | 1 | | | | | | | | | | |
| N,N-Diethyl-m-toluamide | 1 | | | | | | | | | | |
| Ethanol | | | | | | | | | | | |
| Butylene glycol | | | | | | | 1 | | | 2 | 1 |
| Glycerin | | | | | | 3 | 2 | 3 | 2 | | 3 |
| Water/preservative/NaOH | | | | | to 100/q.s./q.s | | | | | | |

APPENDIX

1) Abil ® EM 90
   INCI: Cetyl Dimethicone Copolyol
   Manufacturer: Tego Cosmetics (Goldschmidt)
2) Amphisol ® K
   INCI: Potassium Cetyl Phosphate
   Manufacturer: Hoffmann La Roche
3) Antaron ® V 220
   INCI: PVP/Eicosene Copolymer
   Manufacturer: GAF General Aniline Firm Corp. (IPS-Global)
4) Antaron ® V 216
   INCI: PVP/Hexadecene Copolymer
   Manufacturer: GAF General Aniline Firm Corp. (IPS-Global)
5) Arlacel ® 83
   INCI: Sorbitan Sesquioleate
   Manufacturer: Uniqema (ICI Surfacants)
6) Arlacel ® P 135
   INCI: PEG-30 Dipolyhydroxystearate
   Manufacturer: Uniqema (ICI Surfacants)
7) Bentone ® 38
   INCI: Quaternium-18 Hectorite
   Manufacturer: Rheox (Elementis Specialties)
8) Carbopol ® 980
   INCI: Carbomer
   Manufacturer: Goodrich
9) Carbopol ® 2984
   INCI: Carbomer
   Manufacturer: Goodrich
10) Carbopol ® ETD 2001
    INCI: Carbomer
    Manufacturer: BF Goodrich
11) Carbopol ® Ultrez 10
    INCI: Carbomer
    Manufacturer: Goodrich
12) Cegesoft ® C 17
    INCI: Myristyl Lactate
    Manufacturer: Cognis Deutschland GmbH, Grünau
13) Ceraphyl ® 45
    INCI: Diethylhexyl Malate
    Manufacturer: International Specialty Products
14) Cetiol ® 868
    INCI: Ethylhexyl Stearate
    Manufacturer: Cognis Deutschland GmbH
15) Cetiol ® A
    INCI: Hexyl Laurate
    Manufacturer: Cognis Deutschland GmbH
16) Cetiol ® B
    INCI: Butyl Adipate
    Manufacturer: Cognis Deutschland GmbH (Henkel)
17) Cetiol ® J 600
    INCI: Oleyl Erucate
    Manufacturer: Cognis Deutschland GmbH
18) Cetiol ® OE
    INCI: Dicaprylyl Ether
    Manufacturer: Cognis Deutschland GmbH
19) Cetiol ® PGL
    INCI: Hexyldecanol, Hexyldecyl Laurate
    Manufacturer: Cognis Deutschland GmbH
20) Cetiol ® CC
    INCI: Dicaprylyl Carbonate
    Manufacturer: Cognis Deutschland GmbH
21) Cetiol ® SB 45
    INCI: Shea Butter Butyrospermum Parkii (Linne)
    Manufacturer: Cognis Deutschland GmbH
22) Cetiol ® SN
    INCI: Cetearyl Isononanoate
    Manufacturer: Cognis Deutschland GmbH (Henkel)
23) Cutina ® E 24
    INCI: PEG-20 Glyceryl Stearate
    Manufacturer: Cognis Deutschland GmbH
24) Cutins ® MD
    INCI: Glyceryl Stearate
    Manufacturer: Cognis Deutschland GmbH APPENDIX-continued 25) Dehymuls ® FCE
INCI: Dicocoyl Pentaerythrityl
Distearyl Citrate
Manufacturer: Cognis Deutschland
GmbH
26) Dehymuls ® HRE 7
INCI: PEG-7 Hydrogenated Castor
Oil
Manufacturer: Cognis Deutschland
GmbH
27) Dehymuls ® PGPH
INCI: Polyglyceryl-2
Dipolyhydroxystearate
Manufacturer: Cognis Deutschland
GmbH
28) Dow Corning ® 244 Fluid
INCI: Cyclomethicone
Manufacturer: Dow Corning
29) Dow Corning ® 245 Fluid
INCI: Cyclopentasiloxane
Cyclomethicone
Manufacturer: Dow Corning
30) Dow Corning ® 2502
INCI: Cetyl Dimethicone
Manufacturer: Dow Corning
31) Dry ® Flo Plus
INCI: Aluminium Starch Octenylsuccinate
Manufacturer: National Starch
32) Elfacos ® ST 37
INCI: PEG-22 Dodecyl Glycol Copolymer
Manufacturer: Akzo-Nobel
33) Elfacos ® ST 9
INCI: PEG-45 Dodecyl Glycol Copolymer
Manufacturer: Akzo-Nobel
34) Emery ® 1780
INCI: Lanolin Alcohol
Manufacturer: Cognis Corporation (Emery)
35) Emulgade ® PL 68/50
INCI: Cetearyl Glucoside, Ceteayl Alcohol
Manufacturer: Cognis Deutschland GmbH
36) Emulgade ® SE-PF
INCI: Glyceryl Stearate, Ceteareth-20,
Ceteareth-12, Cetearyl Alcohol, Cetyl
Palmitate
Manufacturer: Cognis Deutschland GmbH
37) Eumulgin ® B 2
INCI: Ceteareth-20
Manufacturer: Cognis Deutschland GmbH
38) Eumulgin ® VL 75
INCI: Lauryl Glucoside (and) Polyglyceryl-2
Dipolyhydroxystearate (and) Glycerin
Manufacturer: Cognis Deutschland
GmbH
39) Eusolex ® OCR
INCI: Octocrylene
Manufacturer: Merck
40) Eusolex ® T 2000
INCI: Titanium Dioxide, Alumina,
Simethicone
Manufacturer: Rona (Merck)
41) Eutanol ® G
INCI: Octyldodecanol
Manufacturer: Cognis Deutschland
GmbH
42) Eutanol ® G 16
INCI: Hexyldecanol
Manufacturer: Cognis Deutschland
GmbH
43) Eutanol ® G 16 S
INCI: Hexyldecyl Stearate
Manufacturer: Cognis Deutschland
GmbH
44) Finsolv ® TN
INCI: C 12/15 Alkyl Benzoate
Manufacturer: Findex
(Nordmann/Rassmann)
45) Generol ® R
INCI: Brassica Campestris
(Rapseed) Sterols
Manufacturer: Cognis Deutschland
GmbH
46) Glucate ® DO
INCI: Methyl Glucose Dioleate
Manufacturer: NRC
Nordmann/Rassmann
47) Hostaphat ® KL 340 N
INCI: Trilaureth-4 Phosphate
Manufacturer: Clariant
48) Isolan ® PDI
INCI: Diisostearoyl Polyglyceryl-3
Diisostearate
Manufacturer: Goldschmidt AG
49) Keltrol ® T
INCI: Xanthan Gum
Manufacturer: CP Kelco
50) Lameform ® TGI
INCI: Polyglyceryl-3 Diisostearate
Manufacturer: Cognis Deutschland GmbH
50) Lanette ® 14
INCI: Myristyl Alcohol
Manufacturer: Cognis Deutschland GmbH
51) Lanette ® E
INCI: Sodium Cetearyl Sulfate
Manufacturer: Cognis Deutschland GmbH
52) Lanette ® O
INCI: Cetearyl Alcohol
Manufacturer: Cognis Deutschland GmbH
53) Monomuls ® 90-0-18
INCI: Glyceryl Oleate
Manufacturer: Cognis Deutschland GmbH
54) Myrj ® 51
INCI: PEG-30-Sterate
Manufacturer: Uniqema
55) Myritol ® 331
INCI: Cocoglycerides
Manufacturer: Cognis Deutschland GmbH
56) Myritol ® PC
INCI: Propylene Glycol
Dicaprylate/Dicaprate
Manufacturer: Cognis Deutschland GmbH
57) Neo Heliopan ® 303
INCI: Octocrylene
Manufacturer: Haarmann & Reimer
58) Neo Heliopan ® AP
INCI: Disodium Phenyl
Dibenzimidazole Tetrasulfonate
Manufacturer: Haarmann & Reimer
59) Neo Heliopan ® AV
INCI: Ethylhexyl Methoxycinnamate
Manufacturer: Haarmann & Reimer
60) Neo Heliopan ® BB
INCI: Benzophenone-3
Manufacturer: Haarmann & Reimer
61) Neo Heliopan ® E 1000
INCI: Isoamyl-p-Methoxycinnamate
Manufacturer: Haarmann & Reimer
62) Neo Heliopan ® Hydro (Na-Salz)
INCI: Phenylbenzimidazole Sulfonic
Acid
Manufacturer: Haarmann & Reimer
63) Neo Heliopan ® MBC
INCI: 4-Methylbenzylidene Camphor
Manufacturer: Haarmann & Reimer
64) Neo Heliopan ® OS
INCI: Ethylhexyl Salicylate
Manufacturer: Haarmann & Reimer
65) Novata ® AB
INCI: Cocoglycerides
Manufacturer: Cognis Deutschland
GmbH
66) Parsol ® 1789
INCI: Butyl
Methoxydibenzoylmethane
Manufacturer: Hoffmann-La Roche
(Givaudan)

APPENDIX-continued

67) Pemulen ® TR-2
   INCI: Acrylates/C10-30 Alkylacrylate Crosspolymer
   Manufacturer: Goodrich
68) Photonyl ® LS
   INCI: Arginine, Disodium Adenosine Triphosphate, Mannitol, Pyridoxine HCL, Phenylalanine, Tyrosine
   Manufacturer: Laboratoires Serobiologiques (Cognis)
69) Prisorine ® ISAC 3505
   INCI: Isostearic Acid
   Manufacturer: Uniqema
70) Prisorine ® 3758
   INCI: Hydrogenated Polyisobutene
   Manufacturer: Uniqema
71) Ravecarb ® 106
   Polycarbonatdiol
   Manufacturer: Enichem
73) SFE ® 839
   INCI: Cyclopentasiloxane and Dimethicone/Vinyl Dimethicone Crosspolymer
   Manufacturer: GE Silicones
74) Silikonöl Wacker AK ® 350
   INCI: Dimethicone
   Manufacturer: Wacker
75) Squatol ® S
   INCI: Hydrogenated Polyisobutene
   Manufacturer: LCW (7-9 rue de l'Industrie 95310 St-Ouen l'Aumone France)
76) Tego ® Care 450
   INCI: Polyglyceryl-3 Methylglucose Distearate
   Manufacturer: Tego Cosmetics (Goldschmidt)
77) Tego ® Care CG 90
   INCI: Cetearyl Glucoside
   Manufacturer: Goldschmidt
78) Tween ® 60
   INCI: Polysorbate 60
   Manufacturer: Uniqema (ICI Surfactants)
79) Uvinul ® T 150
   INCI: Octyl Triazone
   Manufacturer: BASF
80) Veegum ® Ultra
   INCI: Magnesium Aluminium Silicate
   Manufacturer: Vanderbilt
81) Z-Cote ® HP 1
   INCI: Zinc Oxide, Dimethicone
   Manufacturer: BASF

The invention claimed is:

1. A cosmetic composition which is an oil-in-water or water-in-oil emulsion comprising poly-α-olefin oils produced by dehydrating polymerization of 2-ethylhexanol at a temperature in the range of from 60° C. to 340° C. in the presence of acidic alumino layer silicates.

2. The cosmetic composition as claimed in claim 1, wherein said poly-α-olefin oils are hydrogenated after the dehydrating polymerization.

3. The cosmetic composition as claimed in claim 1, further comprising 0.1% to 20% by weight of a surface-active substance or a mixture of surface-active substances.

4. The cosmetic composition of claim 1 containing from 5% to 40% by weight of oil components.

5. The cosmetic composition of claim 1 wherein said poly-α-olefin oils have a high spreading value of >1000 mm$^2$/10 min.

6. The cosmetic composition of claim 1 which comprises 3 to 20% by weight of the poly-α-olefin oils, based on the total quantity of oil components in the composition.

7. The cosmetic composition of claim 1, wherein the dehydrating polymerization is carried out in an inert gas atmosphere.

8. The cosmetic composition of claim 1, further comprising additional oils, fats and/or waxes.

9. A cosmetic composition which is an oil-in-water or water-in-oil emulsion comprising poly-α-olefin oils, produced by dehydrating polymerization of 2-ethylhexanol at a temperature in the range of from 60° C. to 340° C. in the presence of acidic alumino layer silicates, wherein said cosmetic composition comprises 3 to 20% by weight of the poly-α-olefin oils, based on the total quantity of oil components in the composition.

* * * * *